United States Patent
Rotem et al.

(10) Patent No.: US 8,444,630 B2
(45) Date of Patent: *May 21, 2013

(54) OXYGEN SUPPLY FOR CELL TRANSPLANT AND VASCULARIZATION

(75) Inventors: Avi Rotem, Petach-Tikva (IL); Chanan Schneider, Tirat Yehuda (IL); Uriel Barkai, Mp Hof Carmel (IL); Yoav Evron, Hod-Hasharon (IL); Pnina Vardi, Haifa (IL); Konstantin Bloch, Petach-Tikva (IL)

(73) Assignee: Beta-O2 Technologies Ltd., Petach-Tikva (IL)

( * ) Notice: Subject to any disclaimer, the term of this patent is extended or adjusted under 35 U.S.C. 154(b) by 1324 days.

This patent is subject to a terminal disclaimer.

(21) Appl. No.: 12/064,946

(22) PCT Filed: Nov. 28, 2007

(86) PCT No.: PCT/IL2007/001471
§ 371 (c)(1),
(2), (4) Date: Jun. 4, 2008

(87) PCT Pub. No.: WO2008/065660
PCT Pub. Date: Jun. 5, 2008

(65) Prior Publication Data
US 2009/0012502 A1    Jan. 8, 2009

Related U.S. Application Data

(63) Continuation-in-part of application No. 10/466,069, filed on Mar. 12, 2004, now Pat. No. 7,892,222.

(60) Provisional application No. 60/861,592, filed on Nov. 28, 2006.

(51) Int. Cl.
*A61K 9/22* (2006.01)

(52) U.S. Cl.
USPC ........................................ 604/891.1; 604/500

(58) Field of Classification Search
USPC ........... 604/23, 288.01–288.04, 890.1, 891.1, 604/500; 424/93.7, 423
See application file for complete search history.

(56) References Cited

U.S. PATENT DOCUMENTS

| 4,352,883 A | 10/1982 | Lim |
| 4,402,694 A | 9/1983 | Ash et al. |

(Continued)

FOREIGN PATENT DOCUMENTS

| GB | 2024012 | 1/1980 |
| WO | WO-9015526 | 12/1990 |

(Continued)

OTHER PUBLICATIONS

Wu H et al., "In-situ electrochemical oxygen generation with an immunoisolation device", Ann N Y Acad Sci 875:105-25 (1999).

(Continued)

*Primary Examiner* — Theodore Stigell
(74) *Attorney, Agent, or Firm* — Fish & Richardson P.C.

(57) ABSTRACT

Apparatus is provided, including a housing (22), configured for insertion into a body of a patient; a photosynthetic oxygen supply (24) configured to supply oxygen; and functional cells (30), coupled to the housing (22). The functional cells (30) are adapted to receive the oxygen and to secrete at least one factor that induces vascularization in a vicinity of the housing (22) when the housing (22) is in the body of the patient. Other embodiments are also described.

18 Claims, 1 Drawing Sheet

U.S. PATENT DOCUMENTS

| | | | |
|---|---|---|---|
| 4,631,053 A | 12/1986 | Taheri | |
| 4,721,677 A | 1/1988 | Clark, Jr. | |
| 4,801,291 A | 1/1989 | Loori | |
| 5,011,472 A | 4/1991 | Aebischer et al. | |
| 5,029,579 A | 7/1991 | Trammell | |
| 5,101,814 A | 4/1992 | Palti | |
| 5,116,494 A | 5/1992 | Chick et al. | |
| 5,262,055 A | 11/1993 | Bae et al. | |
| 5,336,209 A | 8/1994 | Porzilli | |
| 5,381,075 A | 1/1995 | Jordan | |
| 5,407,685 A | 4/1995 | Malchesky et al. | |
| 5,427,935 A | 6/1995 | Wang et al. | |
| 5,443,508 A | 8/1995 | Giampapa | |
| 5,529,066 A | 6/1996 | Palti et al. | |
| 5,578,022 A | 11/1996 | Scherson et al. | |
| 5,614,378 A | 3/1997 | Yang et al. | |
| 5,662,625 A | 9/1997 | Westwood | |
| 5,702,444 A | 12/1997 | Struthers et al. | |
| 5,713,888 A | 2/1998 | Neuenfeldt et al. | |
| 5,741,334 A | 4/1998 | Mullon et al. | |
| 5,788,682 A | 8/1998 | Maget | |
| 5,792,090 A | 8/1998 | Ladin | |
| 5,834,005 A | 11/1998 | Usala | |
| 5,855,570 A | 1/1999 | Scherson et al. | |
| 5,855,613 A | 1/1999 | Antanavich et al. | |
| 5,879,709 A | 3/1999 | Soon-Shiong et al. | |
| 5,902,745 A | 5/1999 | Butler et al. | |
| 5,912,005 A | 6/1999 | Lanza et al. | |
| 6,000,403 A | 12/1999 | Cantwell | |
| 6,091,974 A | 7/2000 | Palti | |
| 6,148,232 A | 11/2000 | Avrahami | |
| 6,179,804 B1 | 1/2001 | Satterfield | |
| 6,268,161 B1 | 7/2001 | Han et al. | |
| 6,368,592 B1* | 4/2002 | Colton et al. | 424/93.7 |
| 6,372,244 B1 | 4/2002 | Antanavich et al. | |
| 6,383,478 B1 | 5/2002 | Prokop et al. | |
| 6,630,154 B1 | 10/2003 | Fraker et al. | |
| 6,767,342 B1 | 7/2004 | Cantwell | |
| 6,821,107 B1 | 11/2004 | Hara et al. | |
| 6,960,351 B2 | 11/2005 | Dionne et al. | |
| 7,892,222 B2* | 2/2011 | Vardi et al. | 604/891.1 |
| 8,012,500 B2* | 9/2011 | Rotem et al. | 424/423 |
| 8,043,271 B2* | 10/2011 | Stern et al. | 604/288.01 |
| 2003/0050622 A1 | 3/2003 | Humes et al. | |
| 2003/0087427 A1 | 5/2003 | Colton et al. | |
| 2003/0113302 A1 | 6/2003 | Revazova et al. | |
| 2004/0109302 A1 | 6/2004 | Yoneda et al. | |
| 2004/0133188 A1 | 7/2004 | Vardi et al. | |
| 2005/0025680 A1 | 2/2005 | Monzyk et al. | |
| 2005/0136092 A1 | 6/2005 | Rotem et al. | |
| 2006/0024276 A1 | 2/2006 | Ricordi | |
| 2006/0063140 A1 | 3/2006 | Nussinovitch et al. | |
| 2007/0190038 A1 | 8/2007 | Suzuki | |
| 2008/0086042 A1 | 4/2008 | Brister et al. | |
| 2011/0165219 A1 | 7/2011 | Barkai et al. | |

FOREIGN PATENT DOCUMENTS

| | | |
|---|---|---|
| WO | WO9219195 A1 | 11/1992 |
| WO | WO9420076 A1 | 9/1994 |
| WO | WO-0078920 | 12/2000 |
| WO | WO-0150983 | 7/2001 |
| WO | WO-03011445 | 2/2003 |
| WO | WO-2006059322 | 6/2006 |
| WO | 2009031154 | 3/2009 |
| WO | WO2010032242 A1 | 3/2010 |

OTHER PUBLICATIONS

L. Leheninger, Biochemistry, Worth Publishers, Inc. 1978, Chapter 14, pp. 363-364.

Smith AJ, "Acetate assimilation by nitrobacter agilis in relation to its 'obligate autotrophy'", Journal of Bacteriology 95:844 (1968).

Silva AI et al., "An overview on the development of a bio-artificial pancreas as a treatment of insulin-dependent diabetes mellitus," Med Res Rev 26(2); 181-222 (2006).

Faithful, N.S. Anaesthesia, 42, pp. 234-242 (1987).

Lacy PE et al., "Maintenance of normoglycemia in diabetic mice by subcutaneous xenografts of encapsulated islets," Science 1782-4 (1991).

U.S. Appl. No. 60/861,592, filed Nov. 28, 2006.

Kaisers U et al., "Liquid ventilation," British Journal of Anaesthesia 91 (1): 143-151 (2003).

An Office Action dated Jan. 7, 2011, which issued during the prosecution of Applicant's U.S. Appl. No. 11/001,556.

An Interview Summary dated Feb. 28, 2011, which issued during the prosecution of Applicant's U.S. Appl. No. 11/001,556.

An Office Action dated May 31, 2011, which issued during the prosecution of Applicant's Japanese Patent Application No. 2007-544006.

Stagner, et al., "The pancreas as an islet transplantation site", Sep. 1, 2007, Journal of the Pancreas, vol. 8, No. 5, pp. 628-636.

An English Translation of an Office Action dated Dec. 8, 2011, which issued during the prosecution of Japanese Patent Application No. CN 200580047325.4.

An International Search Report dated Jan. 25, 2012, which issued during the prosecution of Applicant's PCT/IL11/00445.

An Office Action dated Mar. 2, 2012 which issued during the prosecution of Japanese Patent Application No. JP 2007-544006.

An Office Action dated May 14, 2012 which issued during the prosecution of U.S. Appl. No. 12/515,818.

* cited by examiner

OXYGEN SUPPLY FOR CELL TRANSPLANT AND VASCULARIZATION

CROSS-REFERENCES TO RELATED APPLICATIONS

The present application is the U.S. national phase of International Application No. PCT/IL2007/001471, filed Nov. 28, 2007, which is a continuation-in-part of U.S. patent application 10/466,069 to Vardi et al., entitled, "Implantable device," filed Mar. 12, 2004 now U.S. Pat. No. 7,892,222; and claims priority from U.S. Provisional Patent Application 60/861,592 to Rotem et al., entitled "Oxygen supply for cell transplant and vascularization," filed Nov. 28, 2006, all of which are incorporated herein by reference. The International Application published in English on Jun. 5, 2008 as WO 2008/065660 under PCT Article 21(2).

FIELD OF THE INVENTION

The present invention relates generally to implantable medical devices. Specifically, the present invention relates to an implantable device to provide oxygen to transplanted cells, e.g., cells in transplanted pancreatic islets.

BACKGROUND OF THE INVENTION

Oxygen is essential to many physiological and metabolic processes, including aerobic metabolism. A lack of oxygen often leads to cell injury or death. Oxygen provision is a vital component in sustaining transplanted cells.

The success of many transplants is compromised not only due to graft-host rejections, but also on account of ischemic conditions generated by insufficient oxygen supply to the transplant.

In healthy individuals, insulin release is regulated so as to maintain blood glucose levels in the range of about 70 to 110 milligrams per deciliter. In diabetics, insulin is either not produced at all (Type I diabetes), or the body cells do not properly respond to the insulin that is produced (Type II diabetes). The result is elevated blood glucose levels.

PCT Publication WO 01/50983 to Vardi et al., and U.S. patent application Ser. No. 10/466,069 in the national phase thereof, which are assigned to the assignee of the present application and are incorporated herein by reference, describe an implantable device comprising a chamber for holding functional cells and an oxygen generator for providing oxygen to the functional cells. In one embodiment, the oxygen generator is described as comprising photosynthetic cells that convert carbon dioxide to oxygen when illuminated. In another embodiment, the oxygen generator is described as comprising electrodes that produce oxygen by electrolysis.

US Patent Application Publication 2005/0136092 to Rotem, which is incorporated herein by reference, describes apparatus including a chamber, which is adapted to be implanted in a body of an individual, the chamber including functional cells and chlorophyll-containing elements comprising chlorophyll of an obligate photoautotroph. Typically, the chlorophyll-containing elements include intact photosynthetic cells and/or isolated chloroplasts. The chlorophyll-containing elements provide oxygen to the functional cells and/or consume carbon dioxide produced by the functional cells. The chamber has one or more walls that are adapted to be permeable to nutrients and substances produced or secreted by the cells. The walls also typically immunoisolate the cells from constituents of the body. The chamber is adapted to be implanted under skin of the subject, or in the peritoneum. The apparatus further comprises a light source that is adapted to provide light to the chlorophyll-containing elements. The chamber may comprise an oxygen sensor that detects an oxygen concentration in a vicinity of the functional cells, and/or in a vicinity of the chlorophyll-containing elements. Providing the light in the series of pulses generally reduces power consumption of the apparatus, and/or provides control of the quantity of oxygen produced by the chlorophyll-containing elements, and/or provides control of the quantity of carbon dioxide consumed by the chlorophyll-containing elements. In some embodiments of the invention, the chamber comprises an oxygen reservoir, which typically comprises a material that stores and releases oxygen, such as responsively to an oxygen concentration in a vicinity of the reservoir. The oxygen reservoir typically stores oxygen produced by the chlorophyll-containing elements that is in excess of the current needs of the functional cells, and releases the stored oxygen if insufficient oxygen is later generated by the chlorophyll-containing elements.

PCT Publication WO 06/059322 to Evron et al., which is incorporated herein by reference, describes apparatus including a chamber which is adapted to be implanted in a body of an individual. The chamber includes functional cells and chlorophyll-containing elements comprising chlorophyll of an obligate photoautotroph. Other embodiments are also described.

U.S. Pat. No. 5,713,888 to Neuenfeldt et al., which is incorporated herein by reference, describes an implant assembly for a host tissue. The implant assembly comprises a pouch including wall means defining a chamber for holding a second member. The wall means includes an outer vascularizing membrane having a conformation that results in growth of vascular structures by the host tissue, close to an interface between the vascularizing membrane and host tissue. The assembly includes a second member that can be removably inserted in the chamber including an interior for receiving cells and wall means defining an immuno-isolating membrane that isolates the cells from the immune response of the host tissue.

U.S. Pat. No. 6,368,592 to Colton et al., which is incorporated herein by reference, describes techniques for supplying oxygen to cells in vitro or in vivo by generating oxygen with an oxygen generator that electrolyzes water to oxygen and hydrogen. The oxygen generator is described as supplying oxygen to cells contained in an encapsulating chamber for implanting in the body, such as an immunoisolation chamber bounded by a semipermeable barrier layer that allows selected components to enter and leave the chamber. A bioactive molecule may be present with the cells.

U.S. Pat. No. 4,721,677 to Clark, Jr. et al., which is incorporated herein by reference, describes an implantable biosensor and method for sensing products, such as hydrogen peroxide, generated from an enzymatic reaction between an analyte, like glucose, and an enzyme in the presence of oxygen. The biosensor is described as being equipped with an enclosed chamber for containing oxygen, and can be adapted for extracting oxygen from animal tissue adjacent the container. The biosensor is designed to optically or electrically sense products generated from the enzymatic reaction, which serve as a function of the analyte.

U.S. Pat. No. 6,960,351 to Dionne et al., which is incorporated herein by reference, describes an immunoisolatory vehicle for the implantation into an individual of cells which produce a needed product or provide a needed metabolic function. The vehicle is comprised of a core region containing isolated cells and materials sufficient to maintain the cells, and a permselective, biocompatible, peripheral region free of the isolated cells, which immunoisolates the core yet provides for the delivery of the secreted product or metabolic function to the individual. The vehicle is described as being particularly well-suited to delivery of insulin from immunoisolated islets of Langerhans, and as being used advantageously for delivery of high molecular weight products, such as products larger than IgG. A method of making a biocompatible, immunoisolatory implantable vehicle is also described, consisting in a first embodiment of a coextrusion process, and in a second embodiment of a stepwise process. A method is described for isolating cells within a biocompatible, immunoisolatory implantable vehicle, which protects the isolated cells from attack by the immune system of an individual in whom the vehicle is implanted. A method is described of providing a needed biological product or metabolic function to an individual, comprising implanting into the individual an immunoisolatory vehicle containing isolated cells which produce the product or provide the metabolic function.

The '351 patent describes a vehicle that provides, in at least one dimension, sufficiently close proximity of any isolated cells in the core to the surrounding tissues of the recipient, including the recipient's bloodstream, in order to maintain the viability and function of the isolated cells. However, the diffusional limitations of the materials used to form the vehicle do not in all cases solely prescribe its configurational limits. Certain additives can be used which alter or enhance the diffusional properties, or nutrient or oxygen transport properties, of the basic vehicle. For example, the internal medium can be supplemented with oxygen-saturated perfluorocarbons, thus reducing the needs for immediate contact with blood-borne oxygen. This is described as allowing isolated cells or tissues to remain viable while, for instance, a gradient of angiotensin is released from the vehicle into the surrounding tissues, stimulating ingrowth of capillaries.

References and methods for use of perfluorocarbons are described in Faithful, N. S. Anaesthesia, 42, pp. 234-242 (1987) and NASA Tech Briefs MSC-21480, U.S. Govt. Printing Office, Washington, D.C. 20402, which are incorporated herein by reference.

US Patent Application Publication 2005/0025680 to Monzyk et al., which is incorporated herein by reference, describes a photolytic cell and a photolytic artificial lung incorporating such a cell. The photolytic artificial lung converts water to oxygen for blood absorption, regulates pH, removes carbon dioxide, and co-produces electrical power. The photolytic artificial lung includes a photolytic cell where all of the chemical reactions occur. Additionally, Monzyk describes photolytically-sensitive materials for oxygen generation. These materials are useful for gas-free artificial lung fabrication. The photolytic cell is described as being useful for directing chemical reactions in organs other than the lung, and for maintaining breathing air in confined systems.

The following patents and patent applications, which are incorporated herein by reference, may be of interest:
 U.S. Pat. No. 5,614,378 to Yang et al.
 U.S. Pat. No. 6,268,161 to Han, et al.
 U.S. Pat. No. 6,383,478 to Prokop, et al.
 U.S. Pat. No. 6,630,154 to Fraker, et al.
 US Patent Application Publication 2003/0113302 to Revazova, et al.
 US Patent Application Publication 2006/0024276 to Ricordi, et al.

The following articles, which are incorporated herein by reference, may be of interest:
 Kaisers U et al., "Liquid ventilation," British Journal of Anaesthesia 91(1):143-151 (2003)
 Lacy P E et al., "Maintenance of normoglycemia in diabetic mice by subcutaneous xenografts of encapsulated islets," Science 1782-4 (1991)
 Silva A I et al., "An overview on the development of a bio-artificial pancreas as a treatment of insulin-dependent diabetes mellitus," Med Res Rev 26(2):181-222 (2006)

SUMMARY OF THE INVENTION

In some embodiments of the present invention, apparatus for containing transplanted cells comprises a housing that is designated for implantation into the body of a patient. The housing is coupled to functional cells, as well as to a limited oxygen supply, which supplies oxygen to the cells. Typically, the oxygen supply is configured to sustain the functional cells for a period of at least twelve hours, e.g., at least several weeks or months, but not for the entire life of the cells within the patient's body. During the period in which the oxygen supply supplies oxygen to the cells, the cells typically secrete factors that induce vascularization in fibrotic tissue surrounding the housing. Once the fibrotic tissue has become vascularized, the transplanted cells generally survive due to oxygen transfer from the newly-vascularized tissue, even after the oxygen supply no longer supplies oxygen.

In an embodiment, the period during which oxygen is supplied is less than one year, less than six months, or less than three months. Typically, the period is between about two weeks and about three months or between about three weeks and about two months, e.g., one month.

As appropriate for a given application, the functional cells and oxygen supply may be disposed within the housing. Alternatively, the oxygen supply is disposed outside of the housing, and is coupled thereto via a small-diameter tube. The functional cells are typically disposed within the housing in a liquid or gel, such as alginate, agarose, or polyethylene glycol (PEG) and/or dispersed in a three-dimensional biodegradable or non-biodegradable fibrillar matrix.

In an embodiment, the oxygen supply comprises a photosynthesizing system such as photosynthesizing algae and a light source, e.g., as described in PCT Publication WO 01/50983 to Vardi et al., or US Patent Application Publication 2005/0136092 to Rotem, which are incorporated herein by reference.

In an embodiment, the oxygen supply comprises an oxygen generator that electrolyzes water to oxygen and hydrogen, e.g., as described in U.S. Pat. No. 6,368,592 to Colton et al., or in PCT Publication WO 01/50983 to Vardi et al., which are incorporated herein by reference.

In some embodiments of the present invention, the oxygen supply comprises a vessel comprising gaseous oxygen. The vessel is typically coupled to provide the oxygen to the functional cells via an oxygen solubilizer such as a gas-permeable silicone rubber membrane.

In an embodiment, the oxygen supply comprises a chemical generator of oxygen, which releases oxygen as a result of a chemical reaction.

For applications in which the functional cells are in islets of Langerhans, the oxygen supply typically supplies oxygen to the islets at a rate of between about 30 and 7,000 micromoles/ hour per 100,000 transplanted islets, e.g., about 500-1,000 micromoles/hour per 100,000 islets, or as otherwise appropriate based on the type and number of functional cells and/or the body weight of the patient. The above-listed oxygen supply rates correspond to the oxygen consumption rate (OCR) of the islets. Typically, the oxygen consumption rate of the islets (having about 2,000 cells per islet) is about 450 picomoles/hour per islet. For example, when the housing comprises one million functional cells (i.e., typically about 500 islets), the oxygen consumption rate is about 150-300 (e.g., 225) nanomoles/hours per million islet cells.

There is therefore provided, in accordance with an embodiment of the present invention, apparatus, including:

a housing, configured for insertion into a body of a patient;
a photosynthetic oxygen supply configured to supply oxygen; and
functional cells, coupled to the housing, and adapted to receive the oxygen and to secrete at least one factor that induces vascularization in a vicinity of the housing when the housing is in the body of the patient.

In an embodiment, the oxygen supply includes:
a light source; and
algae, positioned to receive light from the light source and to generate oxygen by photosynthesis.

In an embodiment, the functional cells includes pancreatic islet cells.

There is further provided, in accordance with an embodiment of the present invention, apparatus, including:

a housing, configured for insertion into a body of a patient;
functional cells, coupled to the housing; and
an oxygen supply, configured to supply oxygen to the functional cells for a period that is no more than 24 months.

In an embodiment, the oxygen supply includes at least one supply selected from the group consisting of: a photosynthetic oxygen generator, a photolytic oxygen generator, a vessel containing gaseous oxygen, a hydrolytic oxygen generator, and a chemical oxygen generator.

In an embodiment, the oxygen supply is configured to supply oxygen to the functional cells for a period that is no more than 12 months.

In an embodiment, the oxygen supply is configured to supply oxygen to the functional cells for a period that is no more than 6 months.

In an embodiment, the oxygen supply is configured to supply oxygen to the functional cells for a period that is no more than 2 months.

There is also provided, in accordance with an embodiment of the invention, apparatus including:

a housing, configured for insertion into a body of a patient;
functional cells, coupled to the housing; and
an oxygen supply, configured to provide to the functional cells between 4 micromoles and 150,000 micromoles of oxygen per million functional cells.

In an embodiment, the functional cells have an oxygen consumption rate of 150-300 nanomoles per hour per million functional cells, and the oxygen supply is configured to provide the oxygen to the functional cells in accordance with the oxygen consumption rate.

In an embodiment, the oxygen supply is configured to provide between 50 micromoles and 15,000 micromoles of oxygen per million functional cells.

In an embodiment, the oxygen supply is configured to provide between 500 micromoles and 10,000 micromoles of oxygen per million functional cells.

In an embodiment, the oxygen supply is configured to supply a quantity of oxygen sufficient to sustain the functional cells for a period of no more than two months.

In an embodiment, the oxygen supply is configured to supply a quantity of oxygen sufficient to sustain the functional cells for a period of no more than one month.

In an embodiment, the oxygen supply is configured to supply a quantity of oxygen sufficient to sustain the functional cells for a period preceding vascularization of tissue around the housing after insertion of the housing into the body of the patient.

In an embodiment, the functional cells include pancreatic islet cells.

In an embodiment, the oxygen supply includes at least one supply selected from the group consisting of: a photosynthetic oxygen generator, a photolytic oxygen generator, a vessel containing gaseous oxygen, a hydrolytic oxygen generator, and a chemical oxygen generator.

In an embodiment, the housing is configured to be positioned subcutaneously inside the body of the patient.

In an embodiment, the oxygen supply is configured to be positioned within the body of the patient.

In an embodiment, the oxygen supply is configured to be positioned outside of the body of the patient.

In an embodiment, the oxygen supply is disposed outside of the housing.

In an embodiment, the oxygen supply is configured to be positioned within the housing.

In an embodiment, the housing includes oxygen solubilizing apparatus.

In an embodiment, the housing includes a biochemical growth factor.

In an embodiment, the housing includes angiogenic factors, e.g., vascular endothelial growth factor (VEGF), basic fibroblast growth factor (bFGF), and/or platelets.

There is yet further provided, in accordance with an embodiment of the present invention, apparatus including:

a housing, configured for insertion into a body of a patient;
pancreatic islets, coupled to the housing; and
an oxygen supply, configured to provide to the pancreatic islets between 800 micromoles and 30 million micromoles of oxygen per 100,000 islets.

In an embodiment, the functional cells have an oxygen consumption rate of 15-30 nanomoles per hour per 100,000 functional cells, and the oxygen supply is configured to provide the oxygen to the functional cells in accordance with the oxygen consumption rate.

In an embodiment, the oxygen supply is configured to provide between 10,000 micromoles and 3 million micromoles of oxygen per 100,000 islets.

In an embodiment, the oxygen supply is configured to provide between 100,000 micromoles and 1.5 million micromoles of oxygen per 100,000 islets.

There is still further provided, in accordance with an embodiment of the present invention, a method including:

implanting functional cells into a body of a patient; and
supplying oxygen to the functional cells for a period that is no more than 24 months.

In an embodiment, implanting the functional cells includes subcutaneously implanting.

In an embodiment, supplying oxygen to the functional cells includes supplying the oxygen for a period that is no more than 12 months.

In an embodiment, supplying oxygen to the functional cells includes supplying the oxygen for a period that is no more than 6 months.

In an embodiment, supplying oxygen to the functional cells includes supplying the oxygen for a period that is no more than 2 months.

In an embodiment, supplying the oxygen includes supplying the oxygen at a rate of between 1 and 10 micromoles/hour per million functional cells.

In an embodiment, supplying the oxygen includes electrolyzing water to oxygen and hydrogen.

In an embodiment, supplying the oxygen includes releasing the oxygen as a result of a chemical reaction.

In an embodiment, supplying the oxygen includes facilitating photosynthesis.

In an embodiment, supplying the oxygen includes performing photolysis.

In an embodiment, supplying the oxygen includes storing the oxygen in gaseous form.

There is additionally provided, in accordance with an embodiment of the present invention, a method including:

implanting, into a body of a patient, functional cells that release a factor that induces vascularization; and inducing the vascularization by supplying oxygen by photosynthesis to the functional cells such that the functional cells release the factor that induces the vascularization.

There is also provided, in accordance with an embodiment of the invention, a method including:

implanting functional cells into a body of a patient; and supplying to the functional cells between 4 micromoles and 150,000 micromoles of oxygen per million functional cells.

In an embodiment, the functional cells have an oxygen consumption rate of 150-300 nanomoles per hour per million functional cells, and the supplying comprises supplying the oxygen to the functional cells in accordance with the oxygen consumption rate.

In an embodiment, supplying includes placing an oxygen supply within the body of the patient.

In an embodiment, supplying includes supplying the oxygen from a site outside of the body of the patient.

In an embodiment, supplying includes supplying oxygen stored as gaseous oxygen.

In an embodiment, supplying includes generating the oxygen within the body of the patient.

In an embodiment, generating the oxygen includes generating the oxygen by a process selected from the group consisting of: photosynthesis, photolysis, electrolysis, and a chemical process.

The present invention will be more fully understood from the following detailed description of embodiments thereof, taken together with the drawings, in which:

DETAILED DESCRIPTION OF THE EMBODIMENTS

Figure 1:
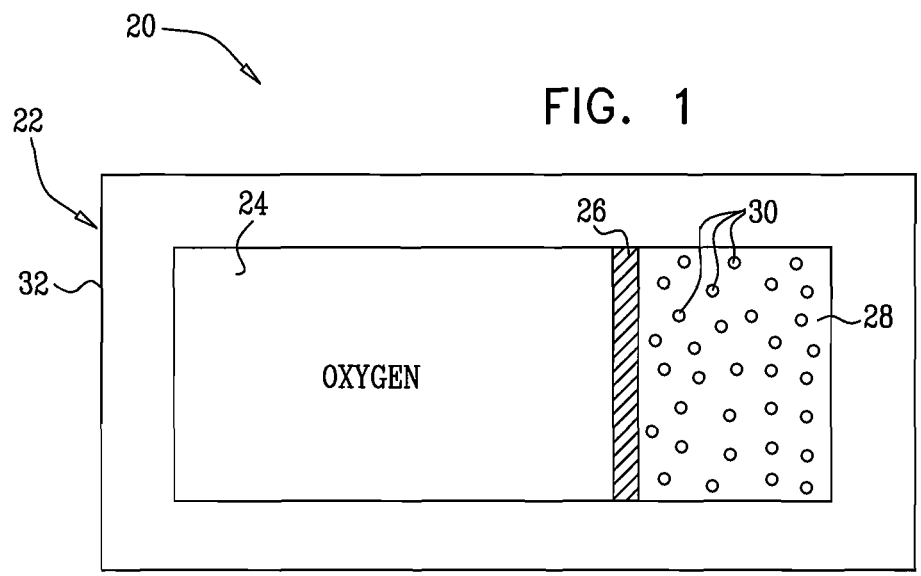
FIG. 1 is a schematic illustration of a housing coupled to functional cells and an oxygen supply, in accordance with an embodiment of the present invention.

Reference is now made to FIG. 1, which is a schematic illustration of apparatus 20 comprising a housing 22 configured for implantation into the body of a patient, e.g., subcutaneously or at another site, in accordance with an embodiment of the present invention. Housing 22 is coupled to functional cells 30, such as pancreatic islet cells that are in islets, and an oxygen supply 24, positioned within housing 20. Typically, oxygen supply 24 generates or contains sufficient oxygen to sustain functional cells 30 during the period preceding vascularization of fibrotic tissue that forms around housing 22. For example, the oxygen supply may generate oxygen in real-time, by photosynthesis (e.g., using algae and an electric light source), photolysis, hydrolysis, or by a chemical reaction. Alternatively or additionally, the oxygen supply comprises a vessel comprising gaseous oxygen. In either case, the oxygen released by oxygen supply 24 typically travels through a gas- and/or water-permeable membrane 26 whereby it enters solution (if necessary) and is uptaken by functional cells 30.

Typically, the real-time generation of oxygen or the total supply of stored oxygen is limited in duration to a quantity that will support the functional cells for a maximum duration that may be as low as several hours, weeks, or months (e.g., 12 hours to one week, or one week to two months) or up to many months (e.g., up to 6, 12, or 24 months). In any case, the oxygen supply typically supports the functional cells for only a small portion of their total lifespan with the patient.

Functional cells 30 are typically disposed within a liquid, gel, and/or fibrillar matrix 28. Housing 22 comprises a selectively-permeable membrane 32 encapsulating either the entire housing, or portions thereof (typically including at least all of cells 30). Membrane 32 is characterized by a molecular cut-off weight of about 11,000-100,000 daltons, that is adapted to allow passage of nutrients and substances produced or consumed by the cells, such as oxygen, carbon dioxide, glucose, insulin, or water. Membrane 32 of housing 22 also typically immunoisolates functional cells 30 by preventing passage therethrough of cells of the patient's body, e.g., white blood cells.

Figure 2:
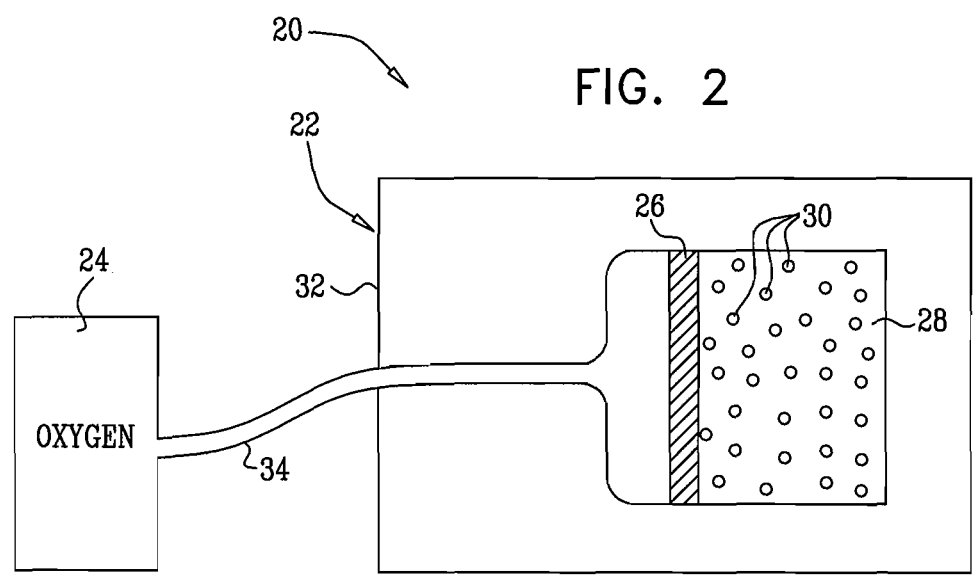
FIG. 2 is a schematic illustration of a housing coupled to functional cells and an oxygen supply, in accordance with another embodiment of the present invention.

Reference is now made to FIG. 2, which is a schematic illustration of apparatus 20 described hereinabove, in accordance with another embodiment of the present invention. In the embodiment shown in FIG. 2, oxygen supply 24 is positioned outside of housing 22, and is coupled thereto by a tube 34. For some applications, supply 24 is disposed within the body of the patient, e.g., at a suitable subcutaneous or other location. Alternatively, the oxygen supply remains outside of the patient's body, and tube 34 transcutaneously couples the oxygen supply to housing 22.

It is to be appreciated that the positioning of oxygen supply 24 shown in FIG. 2 is by way of illustration and not limitation, and that the scope of the present invention includes alignments in close proximity to or far away from housing 22 (rather than adjacent, as shown). Additionally, the scope of the present invention also includes the oxygenation of transplanted cells other than pancreatic islet cells, such as transplanted cells described in references cited in the Background section of the present patent application. For some applications, vascularization around housing 22 is enhanced using one or more biochemical and/or angiogenic factors (e.g., VEGF, bFGF, and/or platelets) coupled to or in a vicinity of housing 22, in addition to or instead of the enhancement of vascularization described above due to secretions by the functional cells.

The scope of the present invention includes embodiments described in one or more of the following:

PCT Patent Application PCT/IL01/00031 to Vardi et al., entitled, "Implantable device," filed Jan. 12, 2001;

U.S. patent application Ser. No. 10/466,069 to Vardi et al., entitled, "Implantable device," filed Mar. 12, 2004;

U.S. patent application Ser. No. 11/001,556 to Rotem et al., entitled "Implantable device," filed Nov. 30, 2004;

PCT Patent Application PCT/IL2005/001262 to Evron et al., entitled, "Implantable device," filed Nov. 27, 2005;

U.S. Provisional Patent Application 60/860,632 to Rotem et al., entitled, "Protecting algae from body fluids," filed Nov. 22, 2006, which is assigned to the assignee of the present patent application and is incorporated herein by reference. For some applications, techniques described in that provisional patent application are performed in combination with techniques described herein;

U.S. Provisional Patent Application 60/861,592 to Rotem et al., entitled, "Oxygen supply for cell transplant and vascularization," filed Nov. 28, 2006; and a US provisional patent application, entitled "Air gaps for supporting cells," to Rozy et al., filed Sep. 7, 2007.

All of these applications are incorporated herein by reference.

For some applications, techniques described herein are practiced in combination with techniques described in one or more of the patent references above, or the references cited in the Cross-references section or Background section of the present patent application, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a housing, configured for insertion into a body of a patient;
a membrane;
functional cells isolated by the membrane and coupled to the housing; and
an oxygen supply, configured to supply oxygen to the functional cells for a period that is no more than 24 months;
wherein the oxygen supply comprises a vessel containing gaseous oxygen, and
wherein the oxygen supply is configured to be disposed outside of the body of the patient and is configured to deliver oxygen transcutaneously to the functional cells in the housing.

2. Apparatus, comprising:
a housing, configured for insertion into a body of a patient;
a membrane;
functional cells isolated by the membrane and coupled to the housing;
a tube; and
an oxygen supply comprising a vessel comprising gaseous oxygen, disposed outside of the body of the patient and configured to transcutaneously supply the gaseous oxygen via the tube to the functional cells.

3. The apparatus according to claim 2, wherein the oxygen supply is configured to house enough oxygen to sustain the functional cells for a period that is at least 12 hours and is no more than 2 months.

4. The apparatus according to claim 2, wherein the oxygen supply is configured to provide between 50 micromoles and 15,000 micromoles of oxygen per million functional cells.

5. The apparatus according to claim 2, wherein the housing is configured to be positioned subcutaneously inside the body of the patient.

6. The apparatus according to claim 2, wherein the housing comprises oxygen solubilizing apparatus.

7. The apparatus according to claim 2, wherein the housing comprises a biochemical growth factor.

8. The apparatus according to claim 2 wherein the functional cell are disposed within pancreatic islets, and wherein the oxygen supply is configured to provide between 10,000 micromoles and 3 million micromoles of oxygen per 100,000 islets.

9. A method, comprising:
implanting functional cells isolated by a membrane into a body of a patient; and
supplying oxygen to the functional cells for a period that is no more than 24 months wherein supplying oxygen to the functional cells comprises transcutaneously supplying oxygen to the functional cells from an oxygen supply that is disposed outside of the body of the patient.

10. A method, comprising:
implanting functional cells isolated by a membrane into a body of a patient; and
supplying oxygen to the functional cells for a period that is no more than 24 months,
wherein supplying comprises supplying to the functional cells between 4 micromoles and 150,000 micromoles of oxygen per million functional cells, and
wherein supplying oxygen to the functional cells comprises transcutaneously supplying oxygen to the functional cells from an oxygen supply that is disposed outside of the body of the patient.

11. A method, comprising:
implanting functional cells isolated by a membrane into a body of a patient; and
transcutaneously supplying gaseous oxygen to the functional cells from a gaseous oxygen supply that is disposed outside the body of the patient.

12. The method according to claim 11, wherein implanting the functional cells comprises subcutaneously implanting.

13. The method according to claim 11, wherein supplying oxygen to the functional cells comprises supplying the oxygen for a period that is no more than 24 months.

14. The method according to claim 11, wherein supplying oxygen to the functional cells comprises supplying the oxygen for a period that is at least 12 hours and is no more than 2 months.

15. The method according to claim 11, further comprising storing the oxygen in gaseous form.

16. The method according to claim 11, wherein supplying comprises supplying oxygen stored as gaseous oxygen.

17. The method according to claim 11, wherein implanting the functional cells comprises implanting functional cells that release a factor that induces vascularization, and wherein the method further comprises inducing the vascularization by supplying oxygen to the functional cells such that the functional cells release the factor that induces the vascularization.

18. The method according to claim 11, wherein implanting the functional cells comprises implanting the functional cells together with one or more factors selected from the group consisting of: a biochemical growth factor, a vascular endothelial growth factor (VEGF), a basic fibroblast growth factor (bFGF), and platelets.

* * * * *